US007268247B2

(12) United States Patent
Zeller

(10) Patent No.: US 7,268,247 B2
(45) Date of Patent: Sep. 11, 2007

(54) PROCESS FOR THE PREPARATION OF PHENYLMALONIC ACID DINITRILES

(75) Inventor: Martin Zeller, Muenchwilen (CH)

(73) Assignee: Syngenta Crop Protection, Inc., Greensboro, NC (US)

(*) Notice: Subject to any disclaimer, the term of this patent is extended or adjusted under 35 U.S.C. 154(b) by 0 days.

(21) Appl. No.: 10/537,408

(22) PCT Filed: Dec. 4, 2003

(86) PCT No.: PCT/EP03/13716

§ 371 (c)(1),
(2), (4) Date: Oct. 5, 2005

(87) PCT Pub. No.: WO2004/050607

PCT Pub. Date: Jun. 17, 2004

(65) Prior Publication Data

US 2006/0135805 A1 Jun. 22, 2006

(30) Foreign Application Priority Data

Dec. 5, 2002 (CH) ................................ 2057/02

(51) Int. Cl.
C07C 255/00 (2006.01)
(52) U.S. Cl. ...................................... 558/357; 558/378
(58) Field of Classification Search ................ 558/302, 558/303, 388, 426
See application file for complete search history.

(56) References Cited

U.S. PATENT DOCUMENTS

| 5,332,720 | A | 7/1994 | Kruger et al. |
| 5,358,924 | A | 10/1994 | Kruger et al. |
| 5,474,974 | A | 12/1995 | Kruger et al. |
| 5,661,110 | A | 8/1997 | Kruger et al. |
| 5,683,965 | A | 11/1997 | Bachmann et al. |
| 5,739,389 | A | 4/1998 | Kruger et al. |
| 5,780,394 | A | 7/1998 | Kruger et al. |
| 6,410,480 | B1 | 6/2002 | Muhlebach et al. |

FOREIGN PATENT DOCUMENTS

| EP | 0508126 | 10/1992 |
| JP | 60197650 | 10/1985 |
| JP | 60204753 | 10/1985 |
| JP | 2000281636 | * 10/2000 |
| WO | 9501971 | 1/1995 |
| WO | 9611574 | 4/1996 |
| WO | 9621652 | 7/1996 |
| WO | 9702243 | 1/1997 |
| WO | 9947525 | 9/1999 |
| WO | 0078712 | * 12/2000 |

OTHER PUBLICATIONS

Chemical Abstracts online citation [retrieved Sep. 26, 2006] Columbus, OH, USA, Uno et al., Tetrahedron Letters (1985), 26(12), 1553-6.*
Zhurnal Organicheskoi Khimii (1992), 28(12), 2541-4 , Chemical Abstracts online citation [retrieved Sep. 26, 2006] Columbus, OH, USA.*
William Adcock and Douglas P Cox: "Electronic nature of the tricyanomethyl group by 13C and 19F NMR: Nature of aryl 19F NMR polar field effects in the benzene and napthalene ring systems"; Journal of Organic Chemistry, vol. 44, No. 17 (1979), pp. 3004-3017; American Chemical Society, Easton, US; ISSN: 0022-3263; p. 3008, examples 2, 3; table 3.
Howard E. Zimmerman and Donald R. Diehl: "Molecular control of excited cross-conjugated triene rearrangements. Exploratory and mechanistic organic photochemistry" Journal of the American Chemical Society, vol. 101, No. 7 (1979), pp. 1841-1857; Journal of the American Chemical Society, vol. 101, No. 7, 1979, pp. 1841-1857, XP002146146.
Ivo Leito et al.:"Spectrophotomeric acidity scale of strong neutral bronsted acids in acetonitrile"; Journal of Organic Chemistry, vol. 63, No. 22 (1998), pp. 7868-7874; XP002146147, American Chemical Society, Easton, US, Issn: 0022-3263.
E. B. Troughton et al.: "Coordination, heterolysis, and electron transfer reactions involving delocalised carbocations and carbanions in solution" Journal of the American Chemical Society, vol. 106, No. 22 (1984) pp. 6726-6735; XP002146148; American Chemical Society, Washington, DC, US; Issn: 0002-7863.
Ilamar A Koppel et al.:"The gas-phase acidities of very strong neutral bronsted acids"; Journal of the American Chemical Society, vol. 116, No. 7 (1994) pp. 3047-3057; XP002146149, American Chemical Society, Washington, DC, US; Issn: 0002-7863.
Winston A Davis and Michael P Cava:"A new synthesis of arylmalononitriles"; Journal of Organic Chemistry, vol. 48 (1983) pp. 2774-2775; XP002146150, American Chemical Society, Easton, US., Issn: 0022-3263.
Rudolf Gompper and Otto Christman:"Neue synthese aromatischer kohlenwasserstoffe", Chemische Berichte, vol. 94 (1961) pp. 1795-1799; XP002146151, Issn: 0009-2940.
Martin R Bryce et al."New electron acceptors: Synthesis, electrochemistry, and radical anions of N, 7,7-tricyanoquinometanimines and X-ray crystal structures of the trimethyl and tetramethyl derivatives"; Journal of Organic Chemistry, vol. 57, No. 6 (1992) pp. 1690-1696; XP002146152, American Chemical Society, Easton, US, Issn: 0022-3263.
Yoshiaki Tsubata et al."Single component organic conductors based on neutral radicals containing the pyrazino-TCNQ skeleton"; Journal of Organic Chemistry, vol. 57, No. 25 (1992) pp. 6749-6755); XP002146153, American Chemical Soceity, Easton, US; Issn: 0022-3263.
M Uno et al."A new route to phenylenedomalononitrile and the analogues, using palladium-catalysed carbon-carbon bond formation" Tetrahedron Letters, vol. 26, No. 12 (1985) pp. 1553-1556; XP002146154, Elsevier Science Publishers, Amsterdam NL; Issn: 0040-4039.
Mitsunari Uno et al, "Palladium-catalysed 1,4-arylation/alkylation of buta-1,3-diene with halogenarenes and stabilised anions"; Journal of the Chemical Society, Perkin Transactions 1 (1990), pp. 647-651; XP002146155, Chemical Society, Letchworth, GB; Issn: 0300-922X.
J. Chem. Soc., Chem. Communication 1984, 932-33.
J. Am. Chem. Soc. 121, 1473-78 (1999).

* cited by examiner

Primary Examiner—Karl Puttlitz
(74) Attorney, Agent, or Firm—Jacqueline Haley

(57) ABSTRACT

Phenylmalonic acid dinitriles are prepared by reaction of, for example, phenyl Kalides with malonic acid dinitrile in the presence of palladium catalysts and bases.

14 Claims, No Drawings

PROCESS FOR THE PREPARATION OF PHENYLMALONIC ACID DINITRILES

This application is the National Stage Application of PCT/EP2003/013716, filed on 4 Dec. 2003 under 35 USC 371, which claims priority to Swiss priority application number 2057/02, filed on 5 Dec. 2002, the contents of both of which are incorporated herein by reference.

The present invention relates to a novel process for the preparation of phenylmalonic acid dinitriles.

Processes for synthesising arylmalonic acid dinitriles by C—C linking of unsubstituted and substituted aryl halides with malonic acid dinitrile are described in Chem. Commun. 1984, 932, JP-A-60 197 650 and WO 00/78712. The syntheses are carried out in the presence of palladium catalysts and bases in inert solvents. There are described as bases especially alkali metal hydrides, alkali metal amides and alkali metal alcoholates.

Surprisingly, it has now been found that the C—C linking of malonic acid dinitrile with mono- or poly-substituted phenyl derivatives can be carried out with a good yield and with a good degree of purity of the phenylmalonic acid dinitriles being prepared when a hydroxide of an alkali metal is employed instead of the bases mentioned in the prior art.

The present invention accordingly relates to a process for the preparation of compounds of formula I

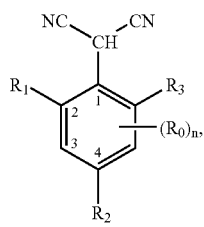

(I)

wherein
each $R_0$, independently of any other(s), is halogen, $C_1$-$C_6$alkyl, $C_2$-$C_6$alkenyl, $C_2$-$C_6$alkynyl $C_1$-$C_6$haloalkyl, cyano-$C_1$-$C_6$alkyl, $C_2$-$C_6$haloalkenyl, cyano-$C_2$-$C_6$alkenyl, $C_2$-$C_6$haloalkynyl, cyano-$C_2$-$C_6$alkynyl, hydroxy, hydroxy-$C_1$-$C_6$alkyl, $C_1$-$C_6$alkoxy, nitro, amino, $C_1$-$C_6$alkylamino, di($C_1$-$C_6$alkyl)amino, $C_1$-$C_6$alkylcarbonylamino, $C_1$-$C_6$alkylsulfonylamino, $C_1$-$C_6$alkylaminosulfonyl, $C_1$-$C_6$alkylcarbonyl, $C_1$-$C_6$alkylcarbonyl-$C_1$-$C_6$alkyl, $C_1$-$C_6$alkoxycarbonyl-$C_1$-$C_6$alkyl, $C_1$-$C_6$alkylcarbonyl-$C_2$-$C_6$alkenyl, $C_1$-$C_6$alkoxycarbonyl, $C_1$-$C_6$alkoxycarbonyl-$C_2$-$C_6$alkenyl, $C_1$-$C_6$alkylcarbonyl-$C_2$-$C_6$alkynyl, $C_1$-$C_6$alkoxycarbonyl-$C_2$-$C_6$alkynyl, cyano, carboxy, phenyl or an aromatic ring containing 1 or 2 hetero atoms selected from the group nitrogen, oxygen and sulfur, wherein the latter two aromatic rings may be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $R_0$, together with the adjacent substituents $R_1$, $R_2$ and $R_3$, forms a saturated or unsaturated $C_3$-$C_6$hydrocarbon bridge that may be interrupted by 1 or 2 hetero atoms selected from the group nitrogen, oxygen and sulfur and/or substituted by $C_1$-$C_4$alkyl;

$R_1$, $R_2$ and $R_3$ are each independently of the others hydrogen, halogen, $C_1$-$C_6$alkyl, $C_2$-$C_6$-alkenyl, $C_2$-$C_6$alkynyl, $C_3$-$C_6$cycloalkyl, $C_1$-$C_6$haloalkyl, $C_2$-$C_6$haloalkenyl, $C_1$-$C_6$alkoxycarbonyl-$C_2$-$C_6$alkenyl, $C_1$-$C_6$alkylcarbonyl-$C_2$-$C_6$alkenyl, cyano-$C_2$-$C_6$alkenyl, nitro-$C_2$-$C_6$-alkenyl, $C_2$-$C_6$haloalkynyl, $C_1$-$C_6$alkoxycarbonyl-$C_2$-$C_6$alkynyl, $C_1$-$C_6$alkylcarbonyl-$C_2$-$C_6$-alkynyl, cyano-$C_2$-$C_6$alkynyl, nitro-$C_2$-$C_6$alkynyl, $C_3$-$C_6$halocycloalkyl, hydroxy-$C_1$-$C_6$alkyl, $C_1$-$C_6$alkoxy-$C_1$-$C_6$alkyl, $C_1$-$C_6$alkylthio-$C_1$-$C_6$alkyl, cyano, $C_1$-$C_4$alkylcarbonyl, $C_1$-$C_6$alkoxycarbonyl, hydroxy, $C_1$-$C_{10}$alkoxy, $C_3$-$C_6$alkenyloxy, $C_3$-$C_6$alkynyloxy, $C_1$-$C_6$haloalkoxy, $C_3$-$C_6$-haloalkenyloxy, $C_1$-$C_6$alkoxy-$C_1$-$C_6$alkoxy, mercapto, $C_1$-$C_6$alkylthio, $C_1$-$C_6$haloalkylthio, $C_1$-$C_6$alkylsulfinyl, $C_1$-$C_6$alkylsulfonyl, nitro, amino, $C_1$-$C_6$alkylamino, di($C_1$-$C_6$alkyl)amino or phenoxy, wherein the phenyl ring may be substituted by $C_1$-$C_3$alkyl, $C_1$-$C_3$haloalkyl, $C_1$-$C_3$-alkoxy, $C_1$-$C_3$haloalkoxy, halogen, cyano or by nitro;

$R_2$ may additionally be phenyl, naphthyl or a 5- or 6-membered aromatic ring that may contain 1 or 2 hetero atoms selected from the group nitrogen, oxygen and sulfur, wherein the phenyl ring, the naphthyl ring and the 5- or 6-membered aromatic ring may be substituted by halogen, $C_3$-$C_8$cycloalkyl, hydroxy, mercapto, amino, cyano, nitro or by formyl; and/or the phenyl ring, the naphthyl ring and the 5- or 6-membered aromatic ring may be substituted by $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$-alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di-$C_1$-$C_6$alkylamino, $C_1$-$C_6$alkylcarbonylamino, $C_1$-$C_6$alkylcarbonyl-($C_1$-$C_6$alkyl)amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$alkenylthio, $C_2$-$C_6$-alkenylsulfinyl, $C_2$-$C_6$alkenylsulfonyl, mono- or di-$C_2$-$C_6$alkenylamino, $C_1$-$C_6$alkyl($C_3$-$C_6$-alkenyl)amino, $C_2$-$C_6$alkenylcarbonylamino, $C_2$-$C_6$alkenylcarbonyl($C_1$-$C_6$alkyl)amino, $C_2$-$C_6$-alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-$C_3$-$C_6$alkynylamino, $C_1$-$C_6$alkyl($C_3$-$C_6$alkynyl)amino, $C_2$-$C_6$alkynylcarbonylamino or by $C_2$-$C_6$alkynylcarbonyl($C_1$-$C_6$alkyl)amino; and/or the phenyl ring, the naphthyl ring and the 5- or 6-membered aromatic ring may be substituted by halo-substituted $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di-$C_1$-$C_6$alkylamino, $C_1$-$C_6$alkylcarbonylamino, $C_1$-$C_6$alkylcarbonyl($C_1$-$C_6$alkyl) amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$alkenylthio, $C_2$-$C_6$alkenylsulfinyl, $C_2$-$C_6$alkenylsulfonyl, mono- or di-$C_2$-$C_6$alkenylamino, $C_1$-$C_6$alkyl-($C_3$-$C_6$alkenyl)amino, $C_2$-$C_6$alkenylcarbonylamino, $C_2$-$C_6$alkenylcarbonyl($C_1$-$C_6$alkyl)amino, $C_2$-$C_6$alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-$C_3$-$C_6$alkynylamino, $C_1$-$C_6$alkyl($C_3$-$C_6$alkynyl)amino, $C_2$-$C_6$alkynylcarbonylamino or $C_2$-$C_6$alkynylcarbonyl($C_1$-$C_6$alkyl)amino; and/or the phenyl ring, the naphthyl ring and the 5- or 6-membered aromatic ring may be substituted by a radical of formula $COOR_{50}$, $CONR_{51}$, $SO_2NR_{53}R_{54}$ or $SO_2OR_{55}$, wherein $R_{50}$, $R_{51}$, $R_{52}$, $R_{53}$, $R_{54}$ and $R_{55}$ are each independently of the others $C_1$-$C_6$alkyl, $C_2$-$C_6$alkenyl or $C_3$-$C_6$alkynyl or halo-, hydroxy-, alkoxy-, mercapto-, amino-, cyano-, nitro-, alkylthio-, alkylsulfinyl- or alkylsulfonyl-substituted $C_1$-$C_6$alkyl, $C_2$-$C_6$alkenyl or $C_3$-$C_6$alkynyl; and n is 0, 1 or 2, by reaction of a compound of formula II

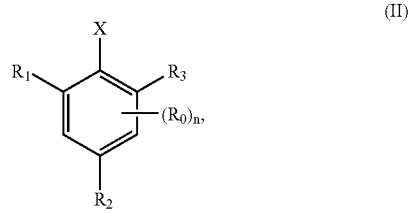

wherein $R_0$, $R_1$, $R_2$, $R_3$ and n are as defined and X is a leaving group, with malonic acid dinitrile in an inert diluent in the presence of a palladium catalyst and a base, which process comprises using as the base a hydroxide of an alkali metal or a mixture of hydroxides of alkali metals.

The present process is distinguished by:
a) high volume concentration of the reactants,
b) the possibility of using a large number of palladium catalysts, which are commercially available or can readily be prepared in situ from commercially available palladium salts, for example palladium(II) chloride solution (20%) in concentrated hydrochloric acid and the appropriate ligands,
c) its ability to be applied especially to phenyl derivatives substituted in the 2- and 6-position as starting compounds, which may contain different and sterically hindered leaving groups,
d) ready availability of the starting compounds,
e) simple reaction procedure,
g) simple working-up and
h) generally very high yields and degrees of purity of the products.

The present preparation process is accordingly suitable especially for the large-scale preparation of arylmalonic acid dinitrile derivatives of formula I.

In the above definitions of the substituents of the compounds of formulae I and II, halogen is to be understood as fluorine, chlorine, bromine or iodine, preferably fluorine, chlorine or bromine.

The alkyl groups in the substituent definitions are, for example, methyl, ethyl, n-propyl, iso-propyl, n-butyl, sec-butyl, isobutyl or tert-butyl, and the pentyl, hexyl, heptyl, octyl, nonyl, decyl, undecyl and dodecyl isomers.

Haloalkyl groups preferably have a chain length of from 1 to 6 carbon atoms. Haloalkyl is, for example, fluoromethyl, difluoromethyl, difluorochloromethyl, trifluoromethyl, chloromethyl, dichloromethyl, dichlorofluoromethyl, trichloromethyl, 2,2,2-trifluoroethyl, 2-fluoroethyl, 2-chloroethyl, 2,2-difluoroethyl, 2,2-dichloroethyl, 2,2,2-trichloroethyl or pentafluoroethyl, preferably trichloromethyl, difluorochloromethyl, difluoromethyl, trifluoromethyl or dichlorofluoromethyl.

Alkoxy groups preferably have a chain length of from 1 to 6 carbon atoms. Alkoxy is, for example, methoxy, ethoxy, n-propoxy, isopropoxy, n-butoxy, isobutoxy, sec-butoxy, tert-butoxy, or the pentyloxy and hexyloxy isomers; preferably methoxy, ethoxy or n-propoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

Examples of alkenyl that may be mentioned are vinyl, allyl, methallyl, 1-methylvinyl, but-2-en-1-yl, pentenyl and 2-hexenyl, with preference being given to alkenyl radicals having a chain length of from 3 to 6 carbon atoms.

Examples of alkynyl that may be mentioned are ethynyl, propargyl, 1-methylpropargyl, 3-butynyl, but-2-yn-1-yl, 2-methylbut-3-yn-2-yl, but-3-yn-2-yl, 1-pentynyl, pent-4-yn-1-yl and 2-hexynyl, with preference being given to alkynyl radicals having a chain length of from 3 to 6 carbon atoms.

As haloalkenyl there come into consideration alkenyl groups substituted one or more times by halogen, halogen being in particular bromine or iodine and especially fluorine or chlorine, for example 2- and 3-fluoropropenyl, 2- and 3-chloropropenyl, 2- and 3-bromopropenyl, 2,2-difluoro-1-methylvinyl, 2,3,3-trifluoropropenyl, 3,3,3-trifluoropropenyl, 2,3,3-trichloropropenyl, 4,4,4-trifluoro-but-2-en-1-yl and 4,4,4-trichloro-but-2-en-1-yl. Of the alkenyl radicals mono-, di- or tri-substituted by halogen, preference is given to those having a chain length of from 3 to 6 carbon atoms. The alkenyl groups may be substituted by halogen at saturated or unsaturated carbon atoms.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

Alkenyloxy is, for example, allyloxy, methallyloxy or but-2-en-1-yloxy.

As haloalkenyloxy there come into consideration alkenyloxy groups substituted one or more times by halogen, halogen being in particular bromine or iodine and especially fluorine or chlorine, for example 2- and 3-fluoropropenyloxy, 2- and 3-chloropropenyloxy, 2- and 3-bromopropenyloxy, 2,3,3-trifluoropropenyloxy, 2,3,3-trichloropropenyloxy, 4,4,4-trifluoro-but-2-en-1-yloxy and 4,4,4-trichloro-but-2-en-1-yloxy.

Alkynyloxy is, for example, propargyloxy or 1-methylpropargyloxy.

Suitable cycloalkyl substituents contain from 3 to 8 carbon atoms and are, for example, cyclopropyl, cyclobutyl, cyclopentyl, cyclohexyl, cycloheptyl or cyclooctyl, each of which may be substituted one or more times by halogen, preferably fluorine, chlorine or bromine.

Alkylcarbonyl is especially acetyl or propionyl.

Alkoxycarbonyl is, for example, methoxycarbonyl, ethoxycarbonyl, n-propoxycarbonyl, iso-propoxycarbonyl or the isomers of butoxycarbonyl, pentyloxycarbonyl and hexyloxycarbonyl; preferably methoxycarbonyl or ethoxycarbonyl.

Alkylthio groups preferably have a chain length of from 1 to 6 carbon atoms. Alkylthio is, for example, methylthio, ethylthio, propylthio, butylthio, pentylthio or hexylthio, or the branched isomers thereof; preferably methylthio or ethylthio.

Haloalkylthio is, for example, 2,2,2-trifluoroethylthio or 2,2,2-trichloroethylthio.

Alkylsulfinyl is, for example, methylsulfinyl, ethylsulfinyl, n-propylsulfinyl, isopropylsulfinyl, n-butylsulfinyl, isobutylsulfinyl, sec-butylsulfinyl or tert-butylsulfinyl; preferably methylsulfinyl or ethylsulfinyl.

Alkylsulfonyl is, for example, methylsulfonyl, ethylsulfonyl, n-propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or the butyl-, pentyl- and hexyl-amino isomers.

Dialkylamino is, for example, dimethylamino, methylethylamino, diethylamino, n-propylmethylamino, dibutylamino or diisopropylamino.

Alkylthioalkyl is, for example, methylthiomethyl, methylthioethyl, ethylthiomethyl, ethylthioethyl, n-propylthiomethyl, n-propylthioethyl, isopropylthiomethyl or isopropylthioethyl.

Phenyl and naphthyl in the definition of $R_2$ and phenoxy in the definiton of $R_1$, $R_2$ and $R_3$ may be in substituted form. The substituents may in that case be in the ortho-, meta- and/or para-positions, as desired, and additionally in the 5-, 6-, 7- and/or 8-positions of the naphthyl ring.

Examples of suitable 5- or 6-membered aromatic rings that contain 1 or 2 hetero atoms selected from the group nitrogen, oxygen and sulfur in the definition of $R_0$ and $R_2$ are pyrrolidyl, pyridyl, pyrimidyl, triazinyl, thiazolyl, triazolyl, thiadiazolyl, imidazolyl, oxazolyl, isoxazolyl, pyrazinyl, furyl, thienyl, pyrazolyl, benzoxazolyl, benzothiazolyl, quinoxalyl, indolyl and quinolyl. These heteroaromatic rings may additionally be substituted.

Definitions corresponding to those given above may also be applied to the substituents in combined definitions, for example alkoxyalkoxy, alkylsulfonylamino, alkylaminosulfonyl, phenylalkyl, naphthylalkyl and heteroarylalkyl.

In the definitions of alkylcarbonyl and alkoxycarbonyl, the carbonyl carbon atom is not included in the lower and upper limits of the number of carbon atoms given in each particular case.

Preference is given to compounds of formula I wherein n is 0, 1 or 2; each $R_0$, independently of any other(s), is halogen, $C_1$-$C_6$alkyl, $C_1$-$C_6$haloalkyl, hydroxy, $C_1$-$C_6$alkoxy, nitro, amino, $C_1$-$C_6$alkylamino, di($C_1$-$C_6$alkyl)amino, $C_1$-$C_6$alkylcarbonylamino, $C_1$-$C_6$alkylsulfonylamino, $C_1$-$C_6$alkylaminosulfonyl, $C_1$-$C_4$alkylcarbonyl, $C_1$-$C_6$alkoxycarbonyl or carboxy; and $R_1$, $R_2$ and $R_3$ are each independently of the others hydrogen, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy-$C_1$-$C_6$alkyl, $C_1$-$C_6$alkylthio-$C_1$-$C_6$alkyl, cyano, $C_1$-$C_4$alkylcarbonyl, $C_1$-$C_6$alkoxycarbonyl, hydroxy, $C_1$-$C_{10}$alkoxy, $C_3$-$C_6$alkenyloxy, $C_3$-$C_6$alkynyloxy, $C_1$-$C_6$haloalkoxy, $C_3$-$C_6$haloalkenyloxy, $C_1$-$C_6$alkoxy-$C_1$-$C_6$alkoxy, mercapto, $C_1$-$C_6$alkylthio, $C_1$-$C_6$haloalkylthio, $C_1$-$C_6$alkylsulfinyl, $C_1$-$C_6$alkylsulfonyl, nitro, amino, $C_1$-$C_4$alkylamino or di($C_1$-$C_4$alkyl)amino.

Preference is given also to compounds of formula I wherein $R_1$, $R_2$ and $R_3$ are each independently of the others hydrogen, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_3$-$C_6$cycloalkyl, $C_1$-$C_4$alkylcarbonyl, $C_1$-$C_6$alkoxycarbonyl, hydroxy, $C_1$-$C_4$alkoxy, $C_3$- or $C_4$-alkenyloxy, $C_3$- or $C_4$-alkynyloxy, $C_1$-$C_4$haloalkoxy, nitro or amino.

Of special importance are compounds of formula I wherein n is 0 and $R_1$, $R_2$ and $R_3$ are each independently of the others $C_1$-$C_4$alkyl.

The preparation of compounds of formula I is illustrated in the following Reaction Scheme 1.

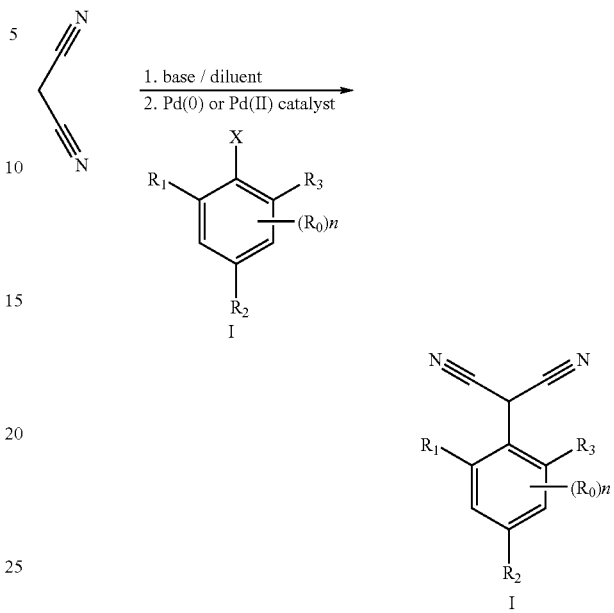

Reaction scheme 1

According to Reaction Scheme 1, the compounds of formula I are obtained from malonic acid dinitrile by reacting the latter in a first reaction step, in a suitable diluent, with a base at a temperature of from 0 to 250° C., preferably at a temperature of from 20 to 100° C., depending on the diluent. In a second reaction step, the C—C linking reaction is carried out by adding compounds of formula II and a palladium catalyst at a temperature of from 0 to 250° C., preferably from 90 to 150° C., depending on the diluent.

The leaving groups X preferred for the C—C linking reaction of the compound of formula II with malonic acid dinitrile in the presence of palladium catalysts are halogen; $R_{10}S(O)_2O$— wherein $R_{10}$ is $C_1$-$C_4$alkyl, preferably methyl, $C_1$-$C_4$haloalkyl, preferably halomethyl or $C_4F_9$-(n), aryl, preferably phenyl, or phenyl substituted from one to three times by halogen, methyl or by halomethyl; and mono-, di- and tri-arylmethoxy.

The aryl radicals of the mono-, di- and tri-arylmethoxy groups are preferably phenyl radicals, which may be substituted, for example, from one to three times by methyl, the substituents preferably being in the 2-, 4- and/or 6-positions of the phenyl ring. Examples of such leaving groups are methylsulfonyloxy (mesylate), trifluoromethylsulfonyloxy (triflate), p-tolylsulfonyloxy (tosylate), $CF_3(CF_2)_3S(O)_2O$— (nonaflate), diphenylmethoxy, di(methylphenyl)methoxy, triphenylmethoxy (trityl) and tri(methylphenyl)methoxy.

Leaving groups that are especially preferred are chlorine, bromine, iodine, $CF_3S(O)_2O$— (triflate), $CF_3(CF_2)_3S(O)_2O$— (nonaflate), p-tolyl-$S(O)_2O$— (tosylate), $(C_6H_5)_2CHO$—, $(CH_3$—$C_6H_4)_2CHO$—, $(C_6H_5)_3CO$— (trityl) and $(CH_3$—$C_6H_4)_3CO$—. Chlorine, bromine and iodine are more especially preferred.

The palladium catalysts that come into consideration for the C—C linking reaction of the compound of formula II with the malonic acid dinitrile anion are generally palladium (II) or palladium(0) complexes, for example palladium(II) dihalides, palladium(II) acetate, palladium(II) sulfate, bis (triphenylphosphine)palladium(II) dichloride, bis(tricyclopentylphosphine)palladium(II) dichloride, bis(tricyclohexylphosphine)palladium(II) dichloride, bis (dibenzylideneacetone)palladium(0) or tetrakis (triphenylphosphine)palladium(0).

In an especially advantageous variant of the process according to the invention, the palladium catalyst can also be prepared in situ from palladium(II) or palladium(0) compounds by complexing with the desired ligands, for example by placing the palladium(II) salt that is to be complexed, for example palladium(II) dichloride ($PdCl_2$) or palladium(II) acetate ($Pd(OAc)_2$), together with the desired ligand, for example triphenylphosphine ($PPh_3$) or tricyclohexylphosphine ($PCy_3$), together with the selected diluent, malonic acid dinitrile and base. Palladium(II) dichloride can be used as an inexpensive palladium salt also in the form of a 20% $PdCl_2$ solution in concentrated hydrochloric acid. The desired ligand is advantageously added to the reaction medium in an excess of up to 10 mol in relation to the palladium salt. By heating the reaction medium, there is then formed in situ the palladium(II) or palladium(0) complex desired for the C—C coupling reaction, which complex then initiates the C—C coupling reaction.

Examples of ligands suitable for palladium(II) and palladium(0) complexes are trimethylphosphine, triethylphosphine, tris(tert-butyl)phosphine, tricyclopentylphosphine, tricyclohexylphosphine ($PCy_3$), tri(methylcyclohexyl)phosphine, methyl(tetramethylene)phosphine, tert-butyl(pentamethylene)phosphine, triphenylphosphine ($PPh_3$), tri(methylphenyl)phosphine, 1,2-diphenylphosphinecyclohexane, 1,2-diphenylphosphinecyclopentane, 2,2'-(diphenylphosphine)-biphenyl, 1,2-bis(diphenylphosphine)ethane, 1,3-bis(diphenylphosphine)propane, 1,4-bis(diphenylphosphine) butane, 3,4-bis(diphenylphosphine)pyrrolidine, 2,2'-(diphenylphosphine)-bisnaphthyl (Binap), 1,1'-bis (diphenylphosphine)ferrocene, 1,1'-bis(di-tert-butylphosphine)ferrocene, diphenyl ether bisdiphenylphosphine

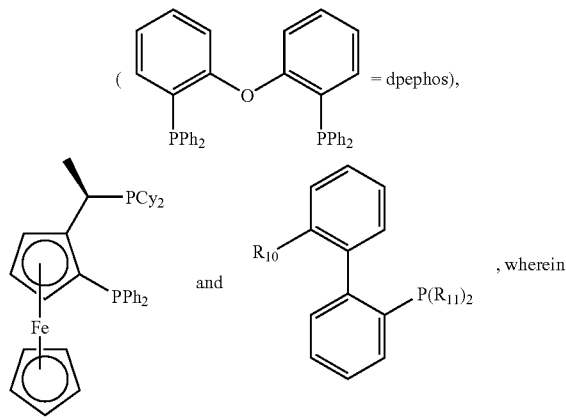

$R_{10}$ is hydrogen or dimethylamino and $R_{11}$ is cyclohexyl or tert-butyl.

Such palladium catalysts are used in an amount of from 0.001 to 100 mol %, especially in an amount of from 0.01 to 10 mol %, and more especially in an amount of from 0.1 to 1 mol %, based on the compound of formula II.

le;.5qDiluents suitable for the formation of the malonic acid dinitrile anion (Step 1) in Reaction Scheme 1) and also for the palladium-catalysed C—C linking reaction with the compound of formula II (Step 2) in Reaction Scheme 1) are aliphatic, cycloaliphatic and aromatic hydrocarbons, for example pentane, hexane, petroleum ether, cyclohexane, methylcyclohexane, benzene, toluene or xylenes, aliphatic halohydrocarbons, for example methylene chloride, chloroform or di- or tetra-chloroethane, nitriles, for example acetonitrile, propionitrile or benzonitrile, ethers, for example diethyl ether, dibutyl ether, tert-butyl methyl ether, ethylene glycol dimethyl ether, ethylene glycol diethyl ether, diethylene glycol dimethyl ether, tetrahydrofuran or dioxane, alcohols, for example methanol, ethanol, propanol, butanol, ethylene glycol, diethylene glycol, ethylene glycol monomethyl or monoethyl ether or diethylene glycol monomethyl or monoethyl ether, ketones, for example acetone or methyl isobutyl ketone, esters or lactones, for example ethyl or methyl acetate or valerolactone, N-substituted lactams, for example N-methylpyrrolidone (NMP), amides, for example N,N-dimethylformamide (DMF) or dimethylacetamide (DMA), acyclic ureas, for example N,N'-dimethylethyleneurea (DMI), sulfoxides, for example dimethyl sulfoxide, or mixtures of such diluents. Of those, special preference is given to aromatic hydrocarbons, ethers, sulfoxides, N-substituted lactams, amides and acyclic ureas.

N-methylpyrrolidone is more especially preferred.

Also suitable as a diluent is water, where appropriate in admixture with one of the above-mentioned diluents.

For the preparation of the malonic acid dinitrile anion there come into consideration, in accordance with the invention, the hydroxides of alkali metals or mixtures of hydroxides of alkali metals, preferably sodium and potassium hydroxide and mixtures of those hydroxides, especially sodium hydroxide.

The base is used preferably in equivalent amounts or in an excess of from 2 to 10 equivalents in relation to malonic acid dinitrile.

The formation of the malonic acid dinitrile anion and reaction thereof with the compound of formula II in the presence of the palladium catalyst is advantageously carried out at reaction temperatures of from 0° to 250° C., preferably at temperatures of from 500 to 200° C., depending on the reaction medium used and the reaction pressure.

If appropriate, the C—C coupling reaction of the malonic acid dinitrile anion with a compound of formula II can be carried out at elevated pressure, preferably at from 1.1 to 10 bar. Such a procedure, carried out in a closed system under elevated pressure, is suitable especially for reactions at temperatures that are above the boiling temperature of the solvent employed, for example at a temperature of 140° C. in the case of toluene.

In view of the very small amount of palladium catalyst (readily decomposable) used for the C—C linking reaction, the catalyst is advantageously metered into the reaction mixture under an inert gas atmosphere and at the very end of the addition sequence of reagents (Step 2) in Reaction Scheme 1).

The compounds of formula II wherein X is, for example, halogen, are known or can be prepared according to known methods, for example a Sandmeyer reaction, from the appropriately substituted anilines of formula VIII

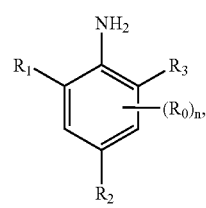

(VIII)

wherein $R_0$, $R_1$, $R_2$, $R_3$ and n are as defined for formula I, via the corresponding diazonium salts.

The compounds of formula II wherein X is, for example, $R_{10}S(O)_2O$— or mono-, di- or tri-arylmethoxy, can be prepared according to standard methods from the corresponding phenols of formula IX

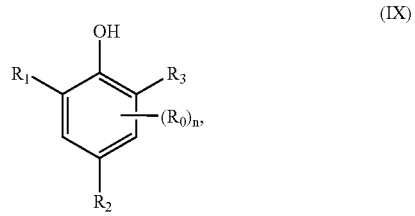

wherein $R_0$, $R_1$, $R_2$, $R_3$ and n are as defined.

The substituted anilines of formula VIII are either known or can be prepared according to known methods, as described, for example, in EP-A-0 362 667, by the alkylation of anilines using olefins.

Similarly, the substituted phenols of formula IX are either known or can be prepared according to customary methods, for example from the corresponding anilines of formula VIII or the diazonium salts thereof by so-called "phenolic boiling".

The following Reaction Scheme 2 illustrates possible processes for the preparation of compounds of formula II.

The substituted aryl dinitriles of formula I are used especially as intermediates in the preparation of substituted 3-hydroxy-4-aryl-5-oxopyrazoline derivatives, which are known, for example, as herbicides from WO 99/47525.

The following Examples illustrate the invention further. They do not limit the invention.

PREPARATION EXAMPLES

Example P1

Preparation of 2-(2,6-diethyl-4-methylphenyl)malonic acid dinitrile

Under a nitrogen atmosphere, 13.9 g of malonic acid dinitrile are added at normal pressure and room temperature to 20.4 g of pulverulent sodium hydroxide in 240 g of 1-methyl-2-pyrrolidone. After the addition of 45.5 g of 2-bromo-1,3-diethyl-5-methylbenzene, the reaction mixture is heated to 125° C. with stirring. At that temperature, a mixture of 1.3 g of triphenylphosphine, 1.06 g of a commercially available palladium(II) chloride solution in concentrated hydrochloric acid (20% Pd content corresponding to 0.354 g of Pd(II) chloride and 0.708 g of concentrated hydrochloric acid) and 97.6 g of 1-methyl-2-pyrrolidone is added. Stirring is carried out for a further 3 hours at from 125 to 130° C., and 283 g of diluent are distilled off at reduced pressure (from 17 to 100 mbar). After cooling to room temperature, the reaction mixture is added to 70 g of water. Following the addition of 38 g of concentrated hydrochloric acid (a pH value of less than 5 is then established), the precipitated solid is filtered off and washed with 60 g of water. After drying, 42.4 g of 2-(2,6-diethyl-4-

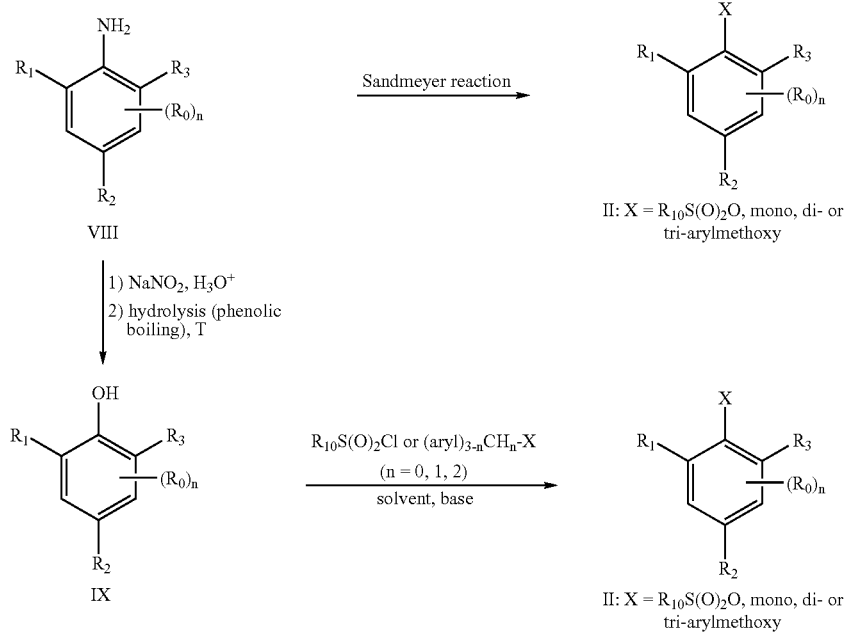

methylphenyl)malonic acid dinitrile (content 92.3%, yield 92.3%) having a melting point of from 74 to 78° C. are obtained.

Example P2

Preparation of 2-(2,6-diethyl-4-methylphenyl)malonic acid dinitrile

Under a nitrogen atmosphere, 14.2 g of malonic acid dinitrile are added at normal pressure and room temperature to a mixture of 48 g of a 50% aqueous solution of sodium hydroxide and 300 g of 1-methyl-2-pyrrolidone. The reaction mixture is heated to from 60 to 100° C., and 98 g of diluent are distilled off under reduced pressure (from 25 to 30 mbar). Under a nitrogen atmosphere, 45.5 g of 2-bromo-1,3-diethyl-5-methylbenzene are added at normal pressure. The reaction mixture is then heated to 130° C. with stirring. At that temperature, a mixture of 0.26 g of triphenylphosphine, 0.2 g of a commercially available palladium(II) chloride solution in concentrated hydrochloric acid (20% Pd content corresponding to 0.071 g of Pd(II) chloride and 0.142 g of concentrated hydrochloric acid) and 19.5 g of 1-methyl-2-pyrrolidone is added. The mixture is stirred at from 125 to 130° C. for a further 3 hours and then 199 g of diluent are distilled off at reduced pressure (from 20 to 25 mbar) at from 90 to 100° C. After cooling to room temperature, the reaction mixture is added to 126 g of water. 4.5 g of Hyflo (Celite) are added thereto, and the mixture is stirred for 30 minutes at 40° C. before being filtered. The filter cake is washed with 114 g of water. Following the addition of 45 g of 32% hydrochloric acid to the filtrate (a pH value of less than 5 is then established), the precipitated solid is filtered off and washed with 120 g of water. After drying, 42.8 g (content 97.3%, yield 98.0%) of 2-(2,6-diethyl-4-methylphenyl)malonic acid dinitrile having a melting point of from 79 to 82° C. are obtained.

Example P3

Preparation of 2-phenylmalonic acid dinitrile

Under a nitrogen atmosphere and at normal pressure, 14 g of malonic acid dinitrile dissolved in 7 ml of 1-methyl-2-pyrrolidone are added dropwise in the course of 30 minutes, at from 20 to 25° C., to a mechanically stirred mixture of 24.1 g of sodium hydroxide (pellets) in 300 ml of 1-methyl-2-pyrrolidone. Evacuation to from 10 to 30 mbar is carried out and, at from 80 to 100° C., approximately 100 ml of solvent are distilled off. After establishing normal pressure, 32 g of bromobenzne are added and the reaction mixture is heated to 125° C. At that temperature, a mixture of 0.26 g of triphenylphosphine, 0.21 g of a commercially available palladium(II) chloride solution in concentrated hydrochloric acid (20% Pd content corresponding to 0.071 g of palladium(II) chloride in 0.142 g of concentrated hydrochloric acid) and 19.5 g of 1-methyl-2-pyrrolidone is added. The reaction mixture is stirred for from 2 to 3 hours at from 125 to 140° C., after which a further 180 ml of solvent is distilled off at from 20 to 60 mbar. 3 g of Hyflo and 150 ml of water are added to the residue which has been cooled to 50° C. The reaction mixture is stirred vigorously for 10 minutes and then clarified by filtration over Hyflo. The filter is subsequently washed with 120 ml of water (divided into 3 portions). The combined aqueous phases are adjusted to a pH <3 using concentrated hydrochloric acid and then extracted with tert-butyl methyl ether (2×200 ml). The organic phases are washed once with water (80 ml), dried over sodium sulfate and concentrated. 27.6 g (95%) of 2-phenylmalonic acid dinitrile, an oil, are obtained, which crystallises out after leaving to stand for some time; m.p. 66-68° C.

The Following are Obtained Analogously to Preparation Example P3:

Starting from 35 g of 4-bromotoluene, 31.2 g (99%) of 2-(p-tolyl)malonic acid dinitrile, m.p. 57-59° C.;

starting from 40.6 g of 2,4,6-trimethylbromobenzene, 37.2 g (98%) of 2-(2,4,5-trimethylphenyl)malonic acid dinitrile, m.p. 91-93° C.;

starting from 37.8 g of 2,6-dimethylbromobenzene, 34 g (96%) of (2,6-dimethylphenyl)malonic acid dinitrile, m.p. 83-85° C. and, starting from 37.4 g of 2-ethylbromobenzene, 25.6 g (72%) of (2-ethylphenyl)malonic acid dinitrile, oil, $n_D^{20}$ 1.518.

Example P4

Preparation of 2-(2,6-diethyl-4-methylphenyl)malonic acid dinitrile

Under a nitrogen atmosphere and at normal pressure, 14 g (217 mmol) of malonic acid dinitrile dissolved in 7 ml of 1-methyl-2-pyrrolidone are added dropwise in the course of 30 minutes, at from 20 to 25° C., to a mechanically stirred mixture of 24.1 g (600 mmol) of sodium hydroxide (pellets) in 300 ml of 1-methyl-2-pyrrolidone. Evacuation to from 10 to 30 mbar is carried out and, at from 80 to 100° C., 113 g of solvent are distilled off. After establishing normal pressure, 48 g (content 94.9%; 200 mmol) of 2-bromo-1,3-diethyl-5-methylbenzene are added and the reaction mixture is heated to 130° C. At that temperature, a mixture of 0.26 g (1 mmol) of triphenylphosphine, 0.21 g of a commercially available palladium(II) chloride solution in concentrated hydrochloric acid (20% Pd content corresponding to 0.071 g (400 μmol) of palladium(II) chloride in 0.142 g of concentrated hydrochloric acid) and 19.5 g of 1-methyl-2-pyrrolidone is added. The reaction mixture is stirred for from 2 to 3 hours at from 125 to 140° C., nitrogen being introduced below the surface. A further 165 g of solvent are distilled off at from 20 to 60 mbar. 2.3 g of Hyflo and 150 ml of water are added to the residue which has been cooled to 50° C. The reaction mixture is stirred vigorously for 10 minutes and then clarified by filtration over Hyflo. The filter is subsequently washed with 55 ml of water. The combined aqueous phases are extracted once with 91 g of toluene. The organic phase is separated off and discarded. 30 g of toluene/water are distilled off from the aqueous phase at from 20 to 70° C. and from 200 to 250 mbar. At from 20 to 25° C. there are added to the distillation sump, in the course of from 60 to 80 minutes, 45.7 g of 32% hydrochloric acid, during the course of which the product crystallises out and the pH value falls to from 4.0 to 4.5. Filtration with suction is carried out, followed by washing with 120 ml of water (divided into 2 portions). The product is dried in a vacuum drying cabinet for 16 hours at from 100 to 250 mbar. 42.2 g (content 98.2%; yield 97.6%) of 2-(2,6-diethyl-4-methylphenyl)malonic acid dinitrile are obtained.

Example P5

Preparation of 2-(2,6-diethyl-4-methylphenyl)malonic acid dinitrile a) Under a nitrogen atmosphere and at normal pressure, 7 g of malonic acid dinitrile dissolved in 3.5 ml of 1-methyl-2-pyrrolidone are added dropwise in the course of 30 minutes, at from 20 to 30° C., to a mechanically stirred mixture of 12 g of sodium hydroxide (pellets) in 150 ml of dimethyl sulfoxide. Evacuation to from 10 to 30 mbar is carried out, and 79.1 g of solvent are distilled off at from 80 to 100° C. After establishing normal pressure, 24 g (content 94.9%) of 2-bromo-1,3-diethyl-5-methylbenzene are added, and the reaction mixture is heated to 130° C. At that temperature, a mixture of 0.13 g of triphenylphosphine, 0.1 g of a commercially available palladium(II) chloride solution in concentrated hydrochloric acid (20% Pd content corresponding to 0.035 g of palladium(II) chloride in 0.071 g of concentrated hydrochloric acid) and 9.6 g of 1-methyl-2-pyrrolidone is added. The reaction mixture is stirred for from 2 to 3 hours at from 125 to 140° C. A further 59.5 g of solvent are distilled off at from 20 to 60 mbar. 1.5 g of Hyflo and 75 ml of water are added to the residue which has been cooled to 50° C. The reaction mixture is stirred vigorously for 10 minutes and then clarified by filtration over Hyflo. The filter is then washed with 50 ml of water. 23.3 g of 32% hydrochloric acid are added to the filtrate in the course of from 60 to 80 minutes, at from 20 to 25° C., during the course of which the product crystallises out and the pH value falls to from 4.0 to 4.5. Suction filtration is carried out, followed by washing with 100 ml of water (divided into 2 portions). The product is dried in a vacuum drying cabinet for 16 hours at from 100 to 250 mbar. 20.6 g (content 97.9%; yield 95.1%) of 2-(2,6-diethyl-4-methylphenyl)malonic acid dinitrile are obtained.

b) Under a nitrogen atmosphere and at normal pressure, 14 g of malonic acid dinitrile dissolved in 7 ml of 1-methyl-2-pyrrolidone are added dropwise in the course of 30 minutes, at from 20 to 30° C., to a mechanically stirred mixture of 24.1 g of sodium hydroxide (pellets) in 300 g of N,N-dimethylacetamide. Evacuation to from 10 to 30 mbar is carried out and, at from 80 to 100° C., 100 g of solvent are distilled off. After establishing normal pressure, 48 g (content 94.9%) of 2-bromo-1,3-diethyl-5-methylbenzene are added and the reaction mixture is heated to 130° C. At that temperature, a mixture of 0.26 g of triphenylphosphine, 0.21 g of a commercially available palladium(II) chloride solution in concentrated hydrochloric acid (20% Pd content corresponding to 0.071 g of palladium(II) chloride in 0.142 g of concentrated hydrochloric acid) and 19.5 g of 1-methyl-2-pyrrolidone is added. The reaction mixture is stirred for from 2 to 3 hours at from 125 to 140° C. A further 181 g of solvent are then distilled off at from 20 to 60 mbar. 2 g of Hyflo and 150 ml of water are added to the residue which has been cooled to 50° C. The reaction mixture is stirred vigorously for 10 minutes and then clarified by filtration over Hyflo. The filter is then washed with 50 ml of water. The combined aqueous phases are extracted once with 91 g of toluene. The organic phase is separated off and discarded. 30 g of toluene/water are distilled off from the aqueous phases at from 20 to 70° C. and from 200 to 250 mbar. 41.3 g of 32% hydrochloric acid are added in the course of from 60 to 80 minutes, at from 20 to 25° C., to the distillation sump, during the course of which the product crystallises out and the pH value falls to from 4.0 to 4.5. Suction filtration is carried out followed by washing with 120 ml of water (divided into 2 portions). The product is dried in a vacuum drying cabinet for 16 hours at from 100 to 250 mbar. 41.9 g of (content 97.8%; yield 96.6%) of 2-(2,6-diethyl-4-methylphenyl)malonic acid dinitrile are obtained.

c) Under a nitrogen atmosphere and at normal pressure, 14 g of malonic acid dinitrile dissolved in 7 ml of 1-methyl-2-pyrrolidone are added dropwise in the course of 30 minutes, at from 20 to 30° C., to a mechanically stirred mixture of 24.1 g of sodium hydroxide (pellets) in 300 g of 1,3-dimethylimidazolidin-2-one. Evacuation to from 10 to 30 mbar is carried out and, at from 80 to 120° C., 136 g of solvent are distilled off. After establishing normal pressure, 48 g (content 94.9%) of 2-bromo-1,3-diethyl-5-methylbenzene are added and the reaction mixture is heated to 130° C. At that temperature, a mixture of 0.26 g of triphenylphosphine, 0.21 g of a commercially available palladium(II) chloride solution in concentrated hydrochloric acid (20% Pd content corresponding to 0.071 g of palladium(II) chloride in 0.142 g of concentrated hydrochloric acid) and 19.5 g of 1-methyl-2-pyrrolidone is added. The reaction mixture is stirred for from 2 to 3 hours at from 125 to 140° C. A further 167 g of solvent are then distilled off at from 20 to 60 mbar. 2 g of Hyflo and 155 ml of water are added to the residue which has been cooled to 50° C. The reaction mixture is stirred vigorously for 10 minutes and then clarified by filtration over Hyflo. The filter is then washed with 50 ml of water. The combined aqueous phases are extracted once with 91 g of toluene. The organic phase is separated off and discarded. 30 g of toluene/water are distilled off from the aqueous phase at from 20 to 70° C. and from 200 to 250 mbar. 42.9 g of 32% hydrochloric acid are added in the course of from 60 to 80 minutes, at from 20 to 25° C., to the distillation sump, during the course of which the product crystallises out and the pH value falls to from 4.0 to 4.5. Suction filtration is carried out followed by washing with 120 ml of water (divided into 2 portions). The product is dried in a vacuum drying cabinet for 16 hours at from 100 to 250 mbar. 41.4 g (content 97.5%; yield 95.2%) of 2-(2,6-diethyl-4-methylphenyl)malonic acid dinitrile are obtained.

Example P6

Preparation of 2-(2,6-diethyl-4-methylphenyl)malonic acid dinitrile

Under a nitrogen atmosphere, 14.2 g of malonic acid dinitrile are added at normal pressure and room temperature to a mixture of 67.3 g of 50% potassium hydroxide solution and 300 ml of 1-methyl-2-pyrrolidone. The reaction mixture is heated to from 60 to 100° C., and 106 g of diluent are distilled off at reduced pressure (from 20 to 30 mbar). Under a nitrogen atmosphere and at normal pressure, 45.5 g of 2-bromo-1,3-diethyl-5-methylbenzene are added. The reaction mixture is then heated to 120° C. with stirring, At that temperature, a mixture of 0.26 g of triphenylphosphine, 0.2 g of a commercially available palladium(II) chloride solution in concentrated hydrochloric acid (20% Pd content corresponding to 0.071 g of palladium(II) chloride and 0.142 g of concentrated hydrochloric acid) and 19.5 g of 1-methyl-2-pyrrolidone is added. Stirring is carried out at from 120 to 125° C. for 1 hour, and then a mixture of 0.26 g of triphenylphosphine, 0.2 g of a commercially available palladium(II) chloride solution in concentrated hydrochloric acid (20% Pd content corresponding to 0.071 g of palladium (II) chloride and 0.142 g of concentrated hydrochloric acid) and 19.5 g of 1-methyl-2-pyrrolidone is again added. The reaction mixture is stirred for 3 hours at from 120 to 125° C., and then a further 237 g of diluent are distilled off at reduced pressure (from 20 to 30 mbar) and at from 80 to 120° C. After cooling the reaction mixture to 45° C., 100 ml of toluene and 220 g of water are added and intensive stirring is carried out for 15 minutes. The two-phase mixture is transferred to a separating funnel in order to be separated. The organic phase is discarded. The aqueous phase is isolated and and 43.4 g of material are distilled off at reduced pressure (from 250 to 300 mbar) and at from 70 to 110° C. 48.5 g of 32% hydrochloric acid are added in the course of from 60 to 80 minutes to the distillation sump, during the course of which the product crystallises out and the pH value falls to from 4.0 to 4.5. Suction filtration is carried out followed by washing with 130 ml of water (divided into 2 portions). The product is dried in a vacuum drying cabinet for 16 hours at from 100 to 250 mbar. 37.2 g (content 97.7%; yield 85.7%) of 2-(2,6-diethyl-4-methylphenyl)malonic acid dinitrile are obtained.

Comparison Test C1

Preparation of
2-(2,6-diethyl-4-methylphenyl)malonic acid dinitrile
using sodium hydride Under a nitrogen atmosphere and at normal pressure, 4.8 g (120 mmol) of 60% sodium hydride are suspended in 60 ml of hexane. The suspension is left to stand. The solvent that separates out is decanted off. 100 g of 1-methyl-2-pyrrolidone are added to the solid and, in the course of 30 minutes, a mixture of 3.7 g (54 mmol) of malonic acid dinitrile and 4 g of 1-methyl-2-pyrrolidone are fed in at room temperature. The mixture is heated to 65° C., and 11.4 g (50 mmol) of 2-bromo-1,3-diethyl-5-methylbenzene are added. The reaction mixture is then heated to from 125 to 130° C. and a mixture of 0.065 g of triphenylphosphine, 0.4 g of a commercially available palladium(II) chloride solution in concentrated hydrochloric acid (20% Pd content corresponding to 0.018 g of palladium(II) chloride in 0.035 g of concentrated hydrochloric acid) and 4.8 g of 1-methyl-2-pyrrolidone is added. The reaction mixture is then stirred for 75 minutes at from 120 to 130° C. A mixture of 0.13 g of triphenylphosphine, 0.1 g of a commercially available palladium(II) chloride solution in concentrated hydrochloric acid (20% Pd content corresponding to 0.035 g of palladium (II) chloride in 0.071 g of concentrated hydrochloric acid) and 9.7 g of 1-methyl-2-pyrrolidone is again added. The reaction mixture is then stirred for 3 hours at from 120 to 130° C. After cooling the mixture to room temperature, 1.3 g of water are added. 100 ml of solvent are then distilled off at reduced pressure (from 20 to 25 mbar) at from 70 to 110° C. 95 g of water and 100 ml of toluene are added to the residue. Intensive stirring is carried out for 30 minutes. The two-phase mixture is separated in a separating funnel. The organic phase is discarded. The aqueous phase is isolated and 30 g of material are distilled off at reduced pressure (from 100 to 150 mbar) and at from 40 to 60° C. 7.7 g of 32% hydrochloric acid are added in the course of from 60 to 80 minutes to the distillation sump, during the course of which the product crystallises out and the pH value falls to from 4.0 to 4.5. Suction filtration is carried out followed by washing with 40 ml of water (divided into 2 portions). The product is dried in a vacuum drying cabinet for 16 hours at from 100 to 250 mbar. 7.7 g (content 98.6%; yield 72%) of 2-(2,6-diethyl-4-methylphenyl)malonic acid dinitrile are obtained.

Comparison Test C2

Preparation of
2-(2,6-diethyl-4-methylphenyl)malonic acid dinitrile
using sodium carbonate Under a nitrogen atmosphere and at normal pressure, 14 g of malonic acid dinitrile dissolved in 7 ml of 1-methyl-2-pyrrolidone are added dropwise in the course of 30 minutes, at from 20 to 25° C., to a mechanically stirred mixture of 64 g of sodium carbonate in 200 ml of 1-methyl-2-pyrrolidone. The reaction mixture is heated to 100° C. and 45.5 g of 2-bromo-1,3-diethyl-5-methylbenzene are added, after which the mixture is heated to 120° C. At that temperature, a mixture of 0.26 g of triphenylphosphine, 0.21 g of a commercially available palladium(II) chloride solution in concentrated hydrochloric acid (20% Pd content corresponding to 0.071 g of palladium(II) chloride in 0.142 g of concentrated hydrochloric acid) and 19.5 g of 1-methyl-2-pyrrolidone is added. The reaction mixture is stirred for from 2 to 3 hours at from 125 to 140° C. A gas chromatogram of a sample (1 ml of reaction mixture partitioned between 2 ml of 1 N hydrochloric acid and 2 ml of tert-butyl methyl ether) shows that the product (2-(2,6-diethyl-4-methylphenyl)malonic acid dinitrile) has not formed.

Comparison Test C3

Preparation of
2-(2,6-diethyl-4-methylphenyl)malonic acid dinitrile
using sodium ethanolate 21.5 g of sodium ethanolate and 150 g of 1-methyl-2-pyrrolidone are mechanically stirred under a nitrogen atmosphere and at normal pressure. 7.3 g of malonic acid dinitrile are added thereto in portions. 58 g of diluent are distilled off at from 100 to 120° C. under reduced pressure (from 20 to 30 mbar). Under a nitrogen atmosphere and at normal pressure, 22.7 g of 2-bromo-1,3-diethyl-5-methylbenzene are added at 110° C. The reaction mixture is heated to 125° C. At that temperature, a mixture of 0.13 g of triphenylphosphine, 0.1 g of a commercially available palladium(II) chloride solution in concentrated hydrochloric acid (20% Pd content corresponding to 0.035 g of palladium(II)chloride in 0.071 g of concentrated hydrochloric acid) and 9.6 g of 1-methyl-2-pyrrolidone is added. The reaction mixture is heated at from 120 to 130° C. for 1 hour. A mixture of 0.13 g of triphenylphosphine, 0.1 g of a commercially available palladium(II) chloride solution in concentrated hydrochloric acid (20% Pd content corresponding to 0.035 g of palladium (II) chloride in 0.071 g of concentrated hydrochloric acid) and 9.6 g of 1-methyl-2-pyrrolidone is again added. The reaction mixture is stirred for 2 hours at from 120 to 130° C. A gas chromatogram of a sample (1 ml of reaction mixture partitioned between 2 ml of 1 N hydrochloric acid and 2 ml of tert-butyl methyl ether) shows that the product (2-(2,6-diethyl-4-methylphenyl)malonic acid dinitrile) has not formed.

What is claimed is:

1. A process for the preparation of a compound of formula I

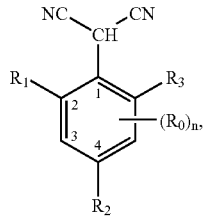

(I)

wherein
each $R_0$, independently of any other(s), is halogen, $C_1$-$C_6$alkyl, $C_2$-$C_6$alkenyl, $C_2$-$C_6$alkynyl, $C_1$-$C_6$-haloalkyl, cyano-$C_1$-$C_6$alkyl, $C_2$-$C_6$haloalkenyl, cyano-$C_2$-$C_6$alkenyl, $C_2$-$C_6$haloalkynyl, cyano-$C_2$-$C_6$alkynyl, hydroxy, hydroxy-$C_1$-$C_6$alkyl, $C_1$-$C_6$alkoxy, nitro, amino, $C_1$-$C_6$alkylamino, di($C_1$-$C_6$alkyl)amino, $C_1$-$C_6$alkylcarbonylamino, $C_1$-$C_6$alkylsulfonylamino, $C_1$-$C_6$alkylaminosulfonyl, $C_1$-$C_6$alkylcarbonyl, $C_1$-$C_6$alkylcarbonyl-$C_1$-$C_6$alkyl, $C_1$-$C_6$alkoxycarbonyl-$C_1$-$C_6$alkyl, $C_1$-$C_6$akylcarbonyl-$C_2$-$C_6$alkenyl, $C_1$-$C_6$alkoxycarbonyl, $C_1$-$C_6$alkoxycarbonyl-$C_2$-$C_6$alkenyl, $C_1$-$C_6$alkylcarbonyl-$C_2$-$C_6$alkynyl, $C_1$-$C_6$alkoxycarbonyl-$C_2$-$C_6$alkynyl, cyano, carboxy, phenyl or an aromatic ring containing 1 or 2 hetero atoms selected from the group nitrogen, oxygen and sulfur, wherein the latter two aromatic rings may be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $R_0$, together with the adjacent substituents $R_1$, $R_2$ and $R_3$, forms a saturated or unsaturated $C_3$-$C_6$hydrocarbon bridge that may be interrupted by 1 or 2 hetero atoms selected from the group nitrogen, oxygen and sulfur and/or substituted by $C_1$-$C_4$alkyl;

$R_1$, $R_2$ and $R_3$ are each independently of the others hydrogen, halogen, $C_1$-$C_6$alkyl, $C_2C_6$alkenyl, $C_2$-$C_6$alkynyl, $C_3$-$C_6$cycloalkyl, $C_1$-$C_6$haloalkyl, $C_2$-$C_6$haloalkenyl, $C_1$-$C_6$alkoxycarbonyl-$C_2$-$C_6$alkenyl, $C_1$-$C_6$alkylcarbonyl-$C_2$-$C_6$alkenyl, cyano-$C_2$-$C_6$alkenyl, nitro-$C_2$-$C_6$alkenyl, $C_2$-$C_6$haloalkynyl, $C_1$-$C_6$alkoxycarbonyl-$C_2$-$C_6$alkynyl, $C_2$-$C_6$alkylcarbonyl-$C_2$-$C_6$alkynyl, cyano-$C_2$-$C_6$alkynyl, nitro-$C_2$-$C_6$alkynyl, $C_3$-$C_6$halocycloalkyl, hydroxy-$C_1$-$C_6$alkyl, $C_1$-$C_6$alkoxy-$C_1$-$C_6$alkyl, $C_1$-$C_6$alkyithio-$C_1$-$C_6$alkyl, cyano, $C_1$-$C_4$alkylcarbonyl, $C_1$-$C_6$alkoxycarbonyl, hydroxy, $C_1$-$C_{10}$alkoxy, $C_3$-$C_6$alkenyloxy, $C_3$-$C_6$alkynyloxy, $C_1$-$C_6$haloalkoxy, $C_3$-$C_6$haloalkenyloxy, $C_1$-$C_6$alkoxy-$C_1$-$C_6$alkoxy, mercapto, $C_1$-$C_6$alkylthio, $C_1$-$C_6$haloalkylthio, $C_1$-$C_6$alkylsulfinyl, $C_1$-$C_6$alkylsulfonyl, nitro, amino, $C_1$-$C_6$alkylamino, di($C_1$-$C_6$alkyl)amino or phenoxy, wherein the phenyl ring may be substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_2$ may additionally be phenyl, naphthyl or a 5- or 6-membered aromatic ring that may contain 1 or 2 hetero atoms selected from the group nitrogen, oxygen and sulfur, wherein the phenyl ring, the naphthyl ring and the 5- or 6-membered aromatic ring may be substituted by halogen, $C_3$-$C_8$cycloalkyl, hydroxy, mercapto, amino, cyano, nitro or by formyl; and/or the phenyl ring, the naphthyl ring and the 5- or 6-membered aromatic ring may be substituted by $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di-$C_1$-$C_6$alkylamino, $C_1$-$C_6$alkylcarbonylamino, $C_1$-$C_6$alkylcarbonyl($C_1$-$C_6$alkyl)amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$alkenylthio, $C_2$-$C_6$alkenylsulfinyl, $C_2$-$C_6$alkenylsulfonyl, mono- or di-$C_2$-$C_6$alkenylamino, $C_1$-$C_6$alkyl($C_3$-$C_6$alkenyl)amino, $C_2$-$C_6$alkenylcarbonylamino, $C_2$-$C_6$alkenylcarbonyl ($C_1$-$C_6$alkyl)amino, $C_2$-$C_6$alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-$C_3$-$C_6$alkynylamino, $C_1$-$C_6$alkyl($C_3$-$C_6$alkynyl)amino, $C_2$-$C_6$alkynylcarbonylamino or by $C_2$-$C_6$alkynylcarbonyl($C_1$-$C_6$alkyl)amino; and/or the phenyl ring, the naphthyl ring and the 5- or 6-membered aromatic ring may be substituted by halo-substituted $C_1$-$C_6$alkyl, $C_1$-$C_6$alkoxy, hydroxy-$C_1$-$C_6$alkyl, $C_1$-$C_6$alkoxy-$C_1$-$C_6$alkyl, $C_1$-$C_6$alkoxy-$C_1$-$C_6$alkoxy, $C_1$-$C_6$alkylcarbonyl, $C_1$-$C_6$alkylthio, $C_1$-$C_6$alkylsulfinyl, $C_1$-$C_6$alkylsulfonyl, mono-$C_1$-$C_6$alkylamino, di-$C_1$-$C_6$alkylamino, $C_1$-$C_6$alkylcarbonylamino, $C_1$-$C_6$alkylcarbonyl($C_1$-$C_6$ alkyl)amino, $C_2$-$C_6$alkenyl, $C_3$-$C_6$alkenyloxy, hydroxy-$C_3$-$C_6$alkenyl, $C_1$-$C_6$alkoxy-$C_2$-$C_6$alkenyl, $C_1$-$C_6$alkoxy-$C_3$-$C_6$alkenyloxy, $C_2$-$C_6$alkenylcarbonyl, $C_2$-$C_6$alkenylthio, $C_2$-$C_6$alkenylsulfinyl, $C_2$-$C_6$alkenylsulfonyl, mono- or di-$C_2$-$C_6$alkenylamino, $C_1$-$C_6$alkyl($C_3$-$C_6$alkenyl)amino, $C_2$-$C_6$alkenylcarbonylamino, $C_2$-$C_6$alkenylcarbonyl ($C_1$-$C_6$alkyl)amino, $C_2$-$C_6$alkynyl, $C_3$-$C_6$alkynyloxy, hydroxy-$C_3$-$C_6$alkynyl, $C_1$-$C_6$alkoxy-$C_3$-$C_6$alkynyl, $C_1$-$C_6$alkoxy-$C_4$-$C_6$alkynyloxy, $C_2$-$C_6$alkynylcarbonyl, $C_2$-$C_6$alkynylthio, $C_2$-$C_6$alkynylsulfinyl, $C_2$-$C_6$alkynylsulfonyl, mono- or di-$C_3$-$C_6$alkynylamino, $C_1$-$C_6$alkyl($C_3$-$C_6$alkynyl) amino, $C_2$-$C_6$alkynylcarbonylamino or $C_2$-$C_6$alkynylcarbonyl($C_1$-$C_6$alkyl)amino; and/or the phenyl ring, the naphthyl ring and the 5- or 6-membered aromatic ring may be substituted by a radical of formula $COOR_{50}$, $CONR_{51}$, $SO_2NR_{53}R_{54}$ or $SO_2OR_{55}$, wherein $R_{50}$, $R_{51}$, $R_{52}$, $R_{53}$, $R_{54}$, and $R_{55}$ are each independently of the others $C_1$-$C_6$alkyl, $C_2$-$C_6$alkenyl or $C_3$-$C_6$alkynyl or halo-, hydroxy-, alkoxy-, mercapto-, amino-, cyano-, nitro-, alkylthio-, alkylsulfinyl- or alkylsulfonyl-substituted $C_1$-$C_6$alkyl, $C_2$-$C_6$alkenyl or $C_3C_6$alkynyl; and n is 0, 1 or 2, by reaction of a compound of formula II

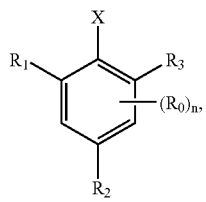

wherein $R_0$, $R_1$, $R_2$, $R_3$ and n are as defined and X is a leaving group, with malonic acid dinitrile in an inert diluent in the presence of a palladium catalyst and a base, which process comprises using as the base a hydroxide of an alkali metal or a mixture of hydroxides of alkali metals and using as the palladium catalyst a palladium(II) dihalide, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0).

2. A process according to claim 1, wherein, in the compound of formula II, X is halogen; $R_{10}S(O)_2O-$ wherein $R_{10}$ is methyl, halomethyl, $C_4F_9$-(n), phenyl or phenyl substituted from one to three times by halogen, methyl or by halomethyl; or is mono-, di- or tri-arylmethoxy.

3. A process according to claim 2, wherein X is chorine, bromine, iodine, $CF_3S(O)_2O$-(triflate), $CF_3(CF_2)_3S(O)_2O$-(nonaflate), p-tolyl-$S(O)_2O$-(tosylate), $(C_6H_5)_2CHO-$, $(CH_3-C_6H_4)_2CHO-$, $(C_6H_5)_3CO$-(trityl) or $(CH_3-C_6H_4)_3CO-$.

4. A process according to claim 3, wherein X is chlorine, bromine or iodine.

5. A process according to claim 1, wherein the palladium catalyst is prepared in situ from palladium(II) or palladium (0) compounds by complexing with phosphine ligands.

6. A process according to claim 1, wherein the palladium catalyst is used in an amount of from 0.001 to 100 mol % based on the compound of formula II.

7. A process according to claim 1, wherein as diluent there is used an aliphatic, cyclo-aliphatic or aromatic hydrocarbon, an aliphatic halohydrocarbon, a nitrile, an ether, an alcohol, a ketone, an ester or a lactone, an N-substituted lactam, an amide, an acyclic urea, a sulfoxide or water or a mixture of those diluents.

8. A process according to claim 7, wherein as an aromatic hydrocarbon there is used an ether, an N-substitued lactam, an amide, an acyclic urea or a sulfoxide.

9. A process according to claim 8, wherein N-methylpyrrolidone is used.

10. A process according to claim 1, wherein as base there is used sodium hydroxide or potassium hydroxide or a mixture of sodium hydroxide and potassium hydroxide.

11. A process according to claim 10, wherein sodium hydroxide is used as the base.

12. A process according to claim 9, wherein the base is used in an equivalent amount or in an excess of from 2 to 10 equivalents in relation to malonic acid dinitrile.

13. A process according to claim 1, wherein the reaction is carried out at a temperature of from 0° to 250° C.

14. A process according to claim 1, wherein the reaction of the malonic acid dinitrile with a compound of formula II is carried out at elevated pressure.

* * * * *